(12) United States Patent
Schlangen et al.

(10) Patent No.: US 9,333,319 B2
(45) Date of Patent: May 10, 2016

(54) ILLUMINATION DEVICE AND METHOD FOR REDUCING SLEEP INERTIA OR CONTROLLING ALERTNESS

(75) Inventors: Lucas Josef Maria Schlangen, Eindhoven (NL); Vanja Hommes, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1241 days.

(21) Appl. No.: 13/263,874

(22) PCT Filed: Apr. 13, 2010

(86) PCT No.: PCT/IB2010/051587
§ 371 (c)(1), (2), (4) Date: Dec. 28, 2011

(87) PCT Pub. No.: WO2010/122446
PCT Pub. Date: Oct. 28, 2010

(65) Prior Publication Data
US 2012/0095534 A1    Apr. 19, 2012

(30) Foreign Application Priority Data
Apr. 16, 2009  (EP) .................................. 09158010

(51) Int. Cl.
*A61N 5/06* (2006.01)
*A61M 21/00* (2006.01)

(52) U.S. Cl.
CPC ........ *A61M 21/00* (2013.01); *A61M 2021/0044* (2013.01); *A61M 2021/0083* (2013.01); *A61N 5/0618* (2013.01)

(58) Field of Classification Search
None
See application file for complete search history.

(56) References Cited

U.S. PATENT DOCUMENTS

| 4,600,723 A | 7/1986 | Short et al. |
| 5,079,682 A * | 1/1992 | Roberts ........................ 362/276 |
| 5,265,598 A | 11/1993 | Searfoss et al. |

(Continued)

FOREIGN PATENT DOCUMENTS

| EP | 2106198 A1 | 9/2009 |
| JP | 11135273 A | 5/1999 |

(Continued)

*Primary Examiner* — Brian T Gedeon

(57) ABSTRACT

The invention relates to a method and an illumination device arranged for reducing sleep inertia and/or for controlling alertness of a human being. The illumination device is arranged for reducing sleep inertia and/or controlling alertness by light radiation. The illumination device comprises one or more light sources for generating a first illumination output and a second illumination output. The first illumination output comprises light with a dominant wavelength in the range of 590-770 nm. The second illumination output comprises light with a dominant wavelength in the range of 400-560 nm. Thus, colored light is used. Alternatively, the first illumination output comprises white light with a color temperature below 4100 K, i.e. warm white light. The second color temperature then comprises white light with a color temperature above 4900 K. The illumination device comprises a controller configured for controlling the one or more light sources to expose said eye of said human being to the first illumination output during a first time interval and to the second illumination output during a second time interval. The second time interval terminates at a later point in time than the first time interval. The time intervals are selected such that at least one of the first and second time interval is less than 60 seconds.

18 Claims, 4 Drawing Sheets

(56) References Cited

U.S. PATENT DOCUMENTS

| | | | |
|---|---|---|---|
| 7,150,710 B2 | 12/2006 | Haber et al. | |
| 7,984,989 B2* | 7/2011 | Gruber | G02C 5/001 351/159.59 |
| 8,427,311 B2* | 4/2013 | Schlangen et al. | 340/540 |
| 8,454,670 B2* | 6/2013 | Chen | A61N 5/0618 607/88 |
| 8,579,795 B2* | 11/2013 | Martel | A61M 21/02 307/10.8 |
| 8,870,740 B2* | 10/2014 | Clegg | A61M 21/00 600/27 |
| 9,138,595 B2* | 9/2015 | Savage | A61M 21/00 |
| 2005/0248962 A1 | 11/2005 | Searfoss, III | |
| 2006/0064144 A1 | 3/2006 | Chen et al. | |
| 2008/0091250 A1 | 4/2008 | Powell | |
| 2008/0103561 A1* | 5/2008 | Moscovici | 607/88 |
| 2008/0119912 A1* | 5/2008 | Hayes | A61M 21/00 607/88 |
| 2009/0281604 A1* | 11/2009 | De Boer | A61M 21/00 607/88 |
| 2011/0125230 A1* | 5/2011 | Friedman | A61N 5/0618 607/90 |

FOREIGN PATENT DOCUMENTS

| | | |
|---|---|---|
| WO | 0220079 A1 | 3/2002 |
| WO | 2008146220 A2 | 12/2008 |

* cited by examiner

ILLUMINATION DEVICE AND METHOD FOR REDUCING SLEEP INERTIA OR CONTROLLING ALERTNESS

FIELD OF THE INVENTION

The invention relates to an illumination device and to a method for reducing sleep inertia and controlling alertness by light radiation.

BACKGROUND OF THE INVENTION

In the last decade the knowledge of human photobiology has increased tremendously in the sense that it is clear that light radiation administered to a human subject through the eye—in addition to vision—is of major importance in controlling a variety of biological rhythms. Consequently, light radiation has not only an influence not only on many physical body functions but also on mental performance and mood.

Findings show a sensitivity of melatonin suppression for light radiation administered through the eye. Melatonin is a hormone showing a daily cycle and is considered a marker of the phase of the biological rhythm. During daytime the melatonin level is relatively low. The melatonin level increases in the evening, and reaches a maximum at night before it decreases gradually again to the minimum level during daytime, i.e. in the period a person normally is awake. Melatonin is generally known as a sleeping hormone that influences the alertness of the human subject. Hence, when the melatonin cycle is controlled, the risk on making mistakes because of lack of alertness is decreased. Suppressing melatonin in the natural daily cycle is possible in the usually 'dark' hours of the biological rhythm. Normally in this period only artificial illumination is available.

In a 24-hour society many people have to work and drive at night and be alert to perform well and safe, and to sleep well at abnormal hours. Under these conditions many people run an enhanced risk of making mistakes, for example causing car accidents, and/or are likely to suffer from a distorted sleeping behavior.

Sleep inertia and alertness dips are undesired from a performance or safety perspective. In general, sleep inertia persists for 30 minutes after waking up. For pilots and military, this persistence of sleep inertia may delay or even endanger operations.

WO 02/20079 discloses a method of controlling alertness of a human subject and a light source for use in this method. The method comprises exposure of a human subject during an exposure period to suitable light radiation. Experiments have shown that there is a particularly high sensitivity to light in the region of 420-460 nm, i.e. in the blue part of the photo spectrum.

SUMMARY OF THE INVENTION

It is an object of the invention to improve the prior art method and light source by enhancing the speed at which stimulating effects of the illumination are experienced.

To that end, an illumination device arranged for reducing sleep inertia and/or controlling alertness by light radiation is disclosed. The illumination device comprises one or more light sources for generating a first illumination output and a second illumination output. The first illumination output comprises light with a dominant wavelength in the range of 590-770 nm. The second illumination output comprises light with a dominant wavelength in the range of 400-560 nm. Thus, colored light is used. Alternatively, the first illumination output comprises white light with a color temperature below 4100 K, i.e. warm white light. The second illumination output then comprises white light with a color temperature above 4900 K, i.e. cold white light. It is possible to combine the alternatives or use the alternatives sequentially. As an example, the first illumination output may comprise a dominant wavelength in the range of 590-770 nm and the second subsequent illumination output may comprises white light with a color temperature above 4900K. Also, the first illumination output may comprise white light with a color temperature below 4100K and the second illumination output may comprise a dominant wavelengths in the range of 400-560 nm. The illumination device also comprises a controller configured for controlling the one or more light sources to expose said eye of said human being to the first illumination output during a first time interval and to the second illumination output during a second time interval. The second time interval terminates at a later point in time than the first time interval. The time intervals are selected such that at least one of the first and second time interval is less than 60 seconds.

The illumination device may be a dedicated device for light therapy, but may also be embodied in another device, such as a decorative illumination device, office lighting, television screens, computer monitors etc. The light sources used in the illumination device can be fluorescent, incandescent, halogen, high intensity discharge (HID), light emitting diodes (LEDs) or other light sources. For such devices, it is advantageous for at least one of the time intervals to be equal to or less than 50 milliseconds to avoid visual discomfort.

Also, a method of reducing sleep inertia and/or controlling alertness of a human being is disclosed. The eye of the human being is exposed to the first illumination output and second illumination output. The second time interval terminates at a later point in time than said first time interval.

Exposing the human being first to the first illumination output as defined above provides for an enhanced effect on the human being to the second illumination output. This enables a reduction of the sleep inertia persistence time and/or a reduction of the time for human to achieve alertness. These effects may e.g. be measured by measuring blinking frequencies of the eye(s) of the exposed person or by eyelid movements (using e.g. the Optalert system, http://www.optalert.com/), reaction time tests, physical activity, EEG, Electro Oculo Gram, heart rate (variability), skin conductance, skin temperature, core body temperature, saliva constituents (cortisol, melatonin, etc.), typing frequency or any other human interaction with a device. Moreover, the enhancement of the effect of the second illumination output due to prior exposure to the first illumination output enables reduction of the required light intensity of that second illumination output, thus improving comfort. By having at least one of the time intervals/periods equal to or less than 60 seconds, the person can be exposed to a relatively frequent variation between the first and second illumination output. Without desiring to be bound by theory, it is believed that such shorter pulses enhance biological activity because the activity is dependent on the differences between the illumination outputs.

It should be appreciated that the first illumination output and the second illumination output may comprise narrowband light or non-narrowband light. Importantly, the dominant wavelength is in the indicated ranges of 590-770 nm and 400-560 nm, respectively.

For narrowband light, the light sources simply have an illumination output in the indicated ranges.

The light source(s) may comprise broadband light sources. For such non-narrowband light sources providing the first and second illumination outputs, a percentage or ratio R of the illumination output in the high and low wavelength ranges of 590-770 nm and 400-560 nm, respectively, over the wavelengths emitted by these non-narrowband light sources to that in the full visible wavelength range of 400-770 nm can be used. Generally, the more light of the illumination output is in the indicated wavelength range, the more effective the irradiation is expected to be.

For the first illumination output, a high wavelength ratio Rhw can be defined as the spectral width Wh in the range of 590-770 nm divided by the spectral width W in the full visible wavelength range of 400-770 nm. Of course, this ratio is 1 for monochromatic light sources with light in the wavelength range of 590-770 nm. Other light sources may comprise a TL16 yellow lamp, typically used in clear rooms having a ratio Rhw of 0.48 or a 2700K 927 or 827 lamp having respective ratios Rhw of 0.57 and 0.51. For the present application, light sources are considered to have a dominant wavelength in the wavelength range of 590-770 nm in case $0.4 \leq Rhw \leq 1$.

Similarly, for the second illumination output, a low wavelength ratio Rlw can be defined as the spectral width Wl in the range of 400-560 nm divided by the spectral width W in the full visible range of 400-770 nm. Again, of course, this ratio Rlw is 1 for monochromatic light sources in the wavelength range of 400-560 nm. Other light sources include 17000 K fluorescent light sources (with a color rendering index of about 80) having Rlw=0.81 or a 4000K fluorescent 840 light source with Rlw=0.57. For the present application, light sources are considered to have a dominant wavelength in the wavelength range of 400-560 nm in case $0.6 \leq Rlw \leq 1$.

It should also be appreciated that for light sources having the first and second illumination outputs with a color temperature below 4100K and above 4900K, the indicated color temperatures may refer to correlated color temperatures in case of light sources deviation from the black body line. When white light is used, the human being is first exposed to warm-white light (color temperature<4100K) and then to cool-white light (color temperature>4900K). The white light is considered more comfortable for the human being, whereas it allows for activities, such as reading of instructions etc., under reasonable light conditions.

In principle a very low intensity of the illumination outputs may already be operative when the human being is dark adapted. For light-adapted human beings a higher intensity will be required.

For the first illumination color output, the lower wavelength limit is chosen since below this wavelength, biological effects such as sleep inertia and/or increased alertness will virtually not be achieved. The upper wavelength limit is provided to avoid exposure of the eye to infrared light. For the second illumination output, the lower wavelength limit is chosen to avoid exposure of the eye to ultraviolet radiation, whereas above the upper wavelength limit, the enhanced effect of the second illumination output is negligible. The embodiment of the invention as defined in claim 2 provides for an optimized combination of the safety and efficiency considerations.

The embodiment of claim 3 provides for a reduced period for overcoming sleep inertia and/or for a rapidly increased alertness as compared to exposure to short-wavelength radiation only. While the first and second time interval may be substantially equally long, the second time interval for exposing the human being to the second illumination output would generally be longer than the first time interval for the first illumination output. At least one of the time intervals, preferably the first time interval, is equal to or less than 60 seconds.

The embodiments of claims 4, 6, 10 and 11 allow for a repeated exposure of the human being to the first and second illumination outputs, thus enhancing the previously described effects.

The embodiment of the invention as defined in claim 5 provides for a rapid alternation of the first and second illumination output at a rate that cannot be followed by the human eye. The human eye will observe a substantially stable average of the first and second illumination outputs, thereby improving comfort.

In the absence of ambient light, the embodiments of claims 7 and 12 allow the inclusion of 'dark' pulses in the series of first and second illumination outputs. Darkness enhances the sensitivity of photoreceptors in the human being's eye for subsequently received light.

The embodiment of the invention as defined in claim 8 provides for an optimal effect of the irradiation.

The parameters for the first and second illumination outputs and the first and second time intervals as defined in claims 2, 3 and 5 may be employed in performing the method as defined in claim 9, as indicated in claims 13 and 14. It is believed that a succession of shorter pulses enhances biological activity rather than longer pulses because the activity is believed, without desiring to be bound to theory, to be dependent on the differences between the illumination outputs. The effects obtained include the reduction of sleep inertia and the increase of alertness of the human being. Further effects include phase shifting (e.g. reducing effects of jet lag, advanced sleep phase syndrome, or delayed sleep phase syndrome) and effects obtained from light therapy, including, but not being limited to, depression treatment (general depression, SAD, etc.).

Mure et al. report in Journal of Biological Rhythms, Vol. 22, No. 5, October 2007, pages 411-424 that pre-stimulation with long wavelength light enhances single-unit responses of SCN neurons to 480 nm light in mice. The mice were submitted to successive 480 nm light stimulations separated by periods of darkness or stimulation with other wavelengths of different durations and irradiances. They find that the efficiency of the light-enhancement effect depends on wavelength, irradiance and duration. The effects are attributed to melanopsin, a photoreceptor in retinal ganglian cells of the mice.

The presence of melanopsin in the human retina was discovered near the end of the last millennium. Berson et al. in Science, Vol. 295, February 2002, pages 1070-1073 first reported the effect of this photoreceptor on the human circadian clock.

These prior art references do not disclose or suggest to reduce sleeping inertia and/or to increase human alertness by the first and second illumination outputs as defined above. The stimulation pulses in the experiments of Mure et al. are significantly longer than 60 seconds, thereby being less efficient than the shorter pulse periods disclosed in the present application.

Hereinafter, embodiments of the invention will be described in further detail. It should be appreciated, however, that these embodiments may not be construed as limiting the scope of protection for the present invention.

DETAILED DESCRIPTION OF THE DRAWINGS

Figure 1A:
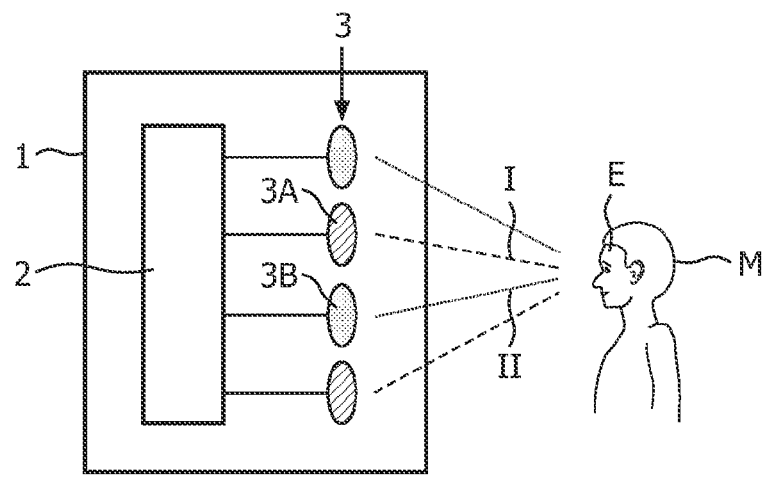
FIG. 1A is a schematic illustration of an illumination device according to an embodiment of the invention.

FIG. 1A is a diagrammatic illustration of an illumination device 1 comprising a controller 2 and a plurality of light sources 3. Illumination device 1 may have a user interface for providing input to controller 2.

The illumination device 1 may be a dedicated device for light therapy, but may also be embodied in another device, such as a decorative illumination device, office lighting, television screens, computer monitors etc. In these other devices, the light sources 3 may have multiple functions, such as displaying images on a display and providing first and second illumination outputs I, II.

Light sources 3A are configured for exposing an eye E of a human being M, to the first illumination output I. The light sources 3A are capable of transmitting the first illumination output I comprising colored light with a dominant wavelength in the range of 590-770 nm, or, more preferably, in a range of 600-650 nm. Alternatively, the first illumination output I may comprise warm white light at a color temperature below 4100 K. In the time diagrams of FIGS. 2A-2F, one or more of the first illumination outputs I may comprise warm-white light.

Light sources 3B are configured for exposing eye E to a second illumination output II. Light sources 3B are capable of transmitting a second illumination output II comprising colored light with a dominant wavelength in the range of 400-560 nm, or, more preferably, in a range of 450-500 nm. Alternatively, the second illumination output II may comprise cool-white white light at a color temperature above 4900K. In the time diagrams of FIGS. 2A-2F, one or more of the second illumination outputs II may comprise cool-white light.

Figure 1B:
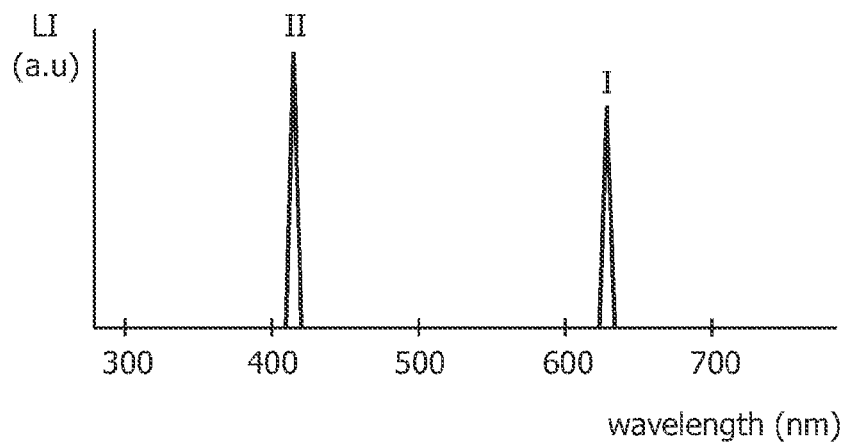
FIGS. 1B and 1C schematically depict spectral distribution diagrams for narrowband and broadband light sources of the illumination device of FIG. 1A.
Figure 1C:
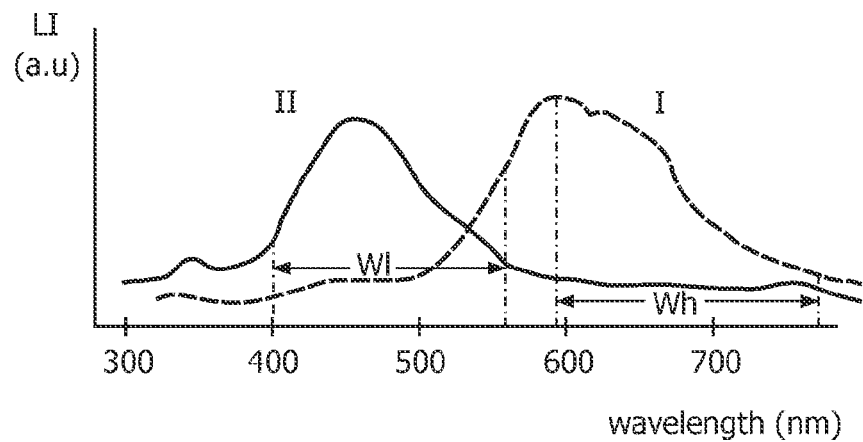

FIGS. 1B and 1C schematically depict spectral distribution diagrams (light intensity LI along the vertical axis and wavelength (nm) along the horizontal axis) for narrowband and broadband light sources 3A, respectively.

For the broadband light sources, as described above, the first illumination output I (dashed line in FIG. 1C) should have a ratio Rhw satisfying 0.4≤Rhw≤1. The spectral width Wh of illumination output I is defined between 590 and 770 nm. Taking the integral over this wavelength region and dividing this by the integral over the full wavelength range of 400-770 nm yields that illumination output I satisfies the above condition for Rhw.

Similarly, for the second illumination output II, the low wavelength ratio Rlw should obey 0.6≤Rlw≤1. The spectral width Wl is defined in the range of 400-560 nm. Taking the integral over this wavelength region and dividing this by the integral over the full wavelength range of 400-770 nm yields that illumination output I satisfies the above condition for Rlw.

The light sources 3 used in the illumination device can be fluorescent, incandescent, halogen, high intensity discharge (HID), light emitting diodes (LEDs) or other light sources. It is noted that a single light source may be capable of providing both the first illumination output I and a second illumination output II. It should also be noted that, e.g. in the embodiment using warm-white light prior to cool-white light, all light sources may contribute to both the first illumination output I and the second illumination output II, wherein the color temperature is varied is response to a signal from the controller 2.

Controller 2 is configured or programmed to determine the time intervals T1, T2 during which, respectively, the first illumination output I and the second illumination output II are provided to the human being M. Generally, the first time interval expires earlier than the second time interval, since the first illumination output as such (i.e. without a subsequent second illumination output) has a substantially zero or even negative effect on the sleep inertia and the alertness of the human being M, while it has positive effects when provided when the human being is at least afterwards exposed to the second illumination output. Therefore, at least part of the exposure to the second illumination output II occurs after exposure of the human being M to the first illumination output I is terminated. Typically, but not necessarily (see FIG. 2D), the first illumination output I starts before the second illumination output II, i.e. the start of the first time interval T1 is prior to the start of the subsequent second time interval T2. At least one of the time intervals T1, T2 is equal to or less than 60 seconds.

Exposing the human being M as described provides for an enhanced effect on the human alertness and reduces sleep inertia. Moreover, the enhancement of the effect of the second illumination output II due to prior exposure to the first illumination output I enables reduction of the required light intensity LI of the second illumination output, thus improving comfort.

FIGS. 2A-2F are time diagrams illustrating several embodiments of a method of exposing a human being M to first and second illumination outputs I, II using the illumination device 1 of FIG. 1A. The vertical axis of the time diagrams denotes the light intensity LI to which the human being M is exposed in arbitrary units. The horizontal axis denotes the time (in seconds or minutes). Timing and light intensity of the illumination outputs I, II are regulated by controller 2 and may be pre-programmed in a memory of the illumination device 1 or be input via a user interface of illumination device 1. It should be appreciated that many alternative embodiments can be envisaged by a skilled person without departing from the gist of the present invention.

Figure 2A:
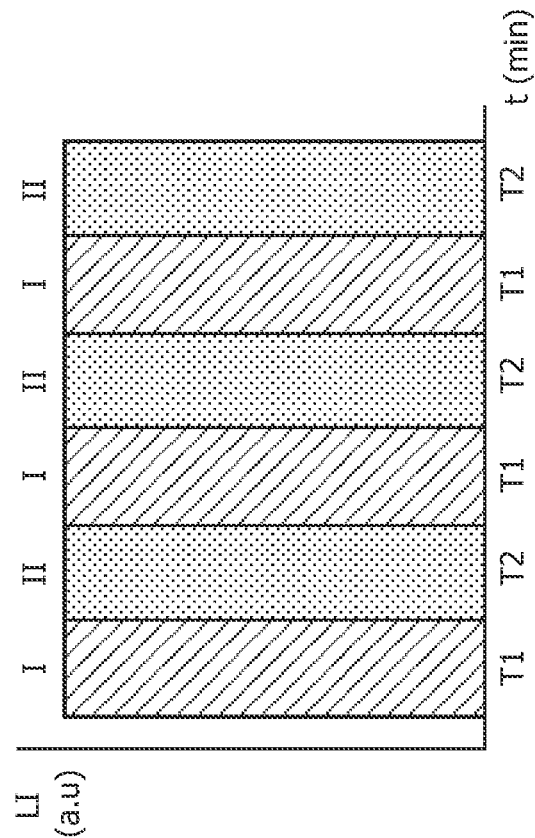
FIGS. 2A-2F are time diagrams illustrating several embodiments of a method of exposing a human being to light of the illumination device of FIG. 1A.

FIG. 2A illustrates a basic embodiment of the invention wherein a first illumination output I is provided during a first time interval T1 prior to a second illumination output II during a time interval T2, here being equal to T1. T1 and T2 may e.g. be 60 seconds each. Of course, first illumination output I may also be provided directly prior to the second illumination output II, i.e. without a delay.

Figure 2B:
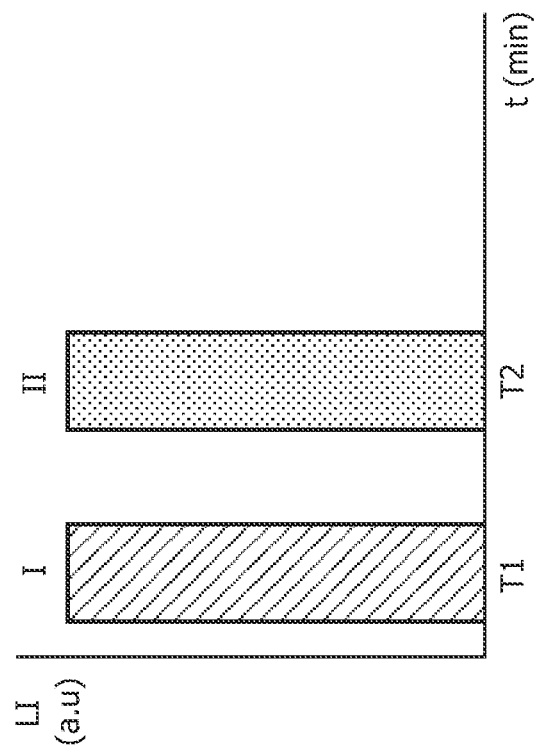

FIG. 2B shows a time diagram wherein first and second illumination outputs I, II are alternated. T1 and T2 may e.g. be 60 seconds each. Alternatively, both T1 and T2 have a duration of only 50 milliseconds. Such a rapid alternation of the first and second illumination output cannot be followed by the human eye. The human eye will observe a substantially stable average of the first and second illumination outputs, thereby improving comfort.

Figure 2D:
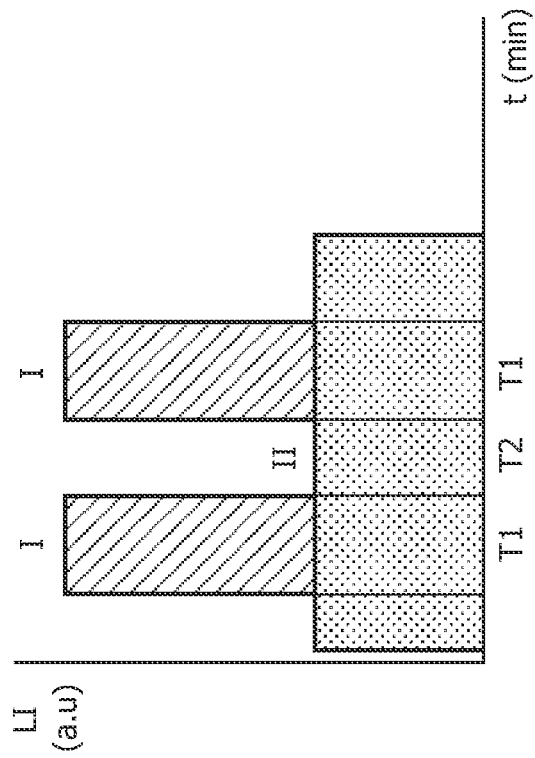
Figure 2C:
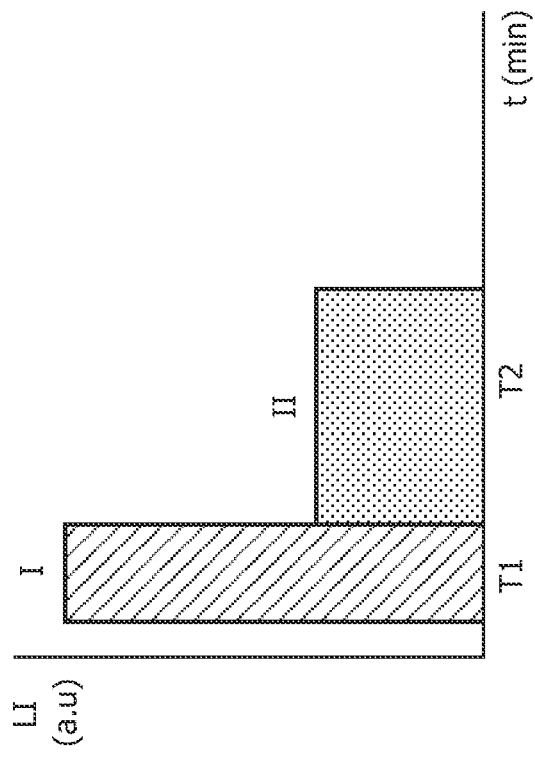

FIG. 2C shows a time diagram wherein a first illumination output I is provided during a first time interval T1 prior to a second illumination output II during a time interval T2. The second interval T2 is significantly longer than the first time interval T1. As an example, time interval T1 has a duration of 60 seconds, 10 seconds, 1 second, 100 milliseconds, 10 milliseconds or 1 millisecond and time interval T2 has a duration of 10 minutes, 1 minute or 1 second. The light intensity LI of the second illumination output II is lower than the light intensity LI of the first illumination output I. Time intervals T1 and T2 may be repeated.

FIG. 2D shows a time diagram wherein first illumination outputs I are provided during first time intervals T1 within the second time interval T2 of second illumination output II. Controller 2 controls light sources 3 such that human being M is continuously exposed to light sources 3B during time interval T2, providing e.g. blue light, whereas light sources 3A generate red light during the first time intervals T1 for increasing the efficiency of the blue light exposure (while also being exposed to second illumination output). Time interval T2 has a duration of e.g. 10 minutes, whereas time intervals T1 have a duration of e.g. 60 or 30 seconds. It is noted that, alternatively, time interval T1 may have a duration longer than 60 seconds and time interval T2 may be less that 60 seconds. Furthermore, it should be noted that the intensity and duration of the first and/or second illumination output need not remain constant.

Figure 2E:
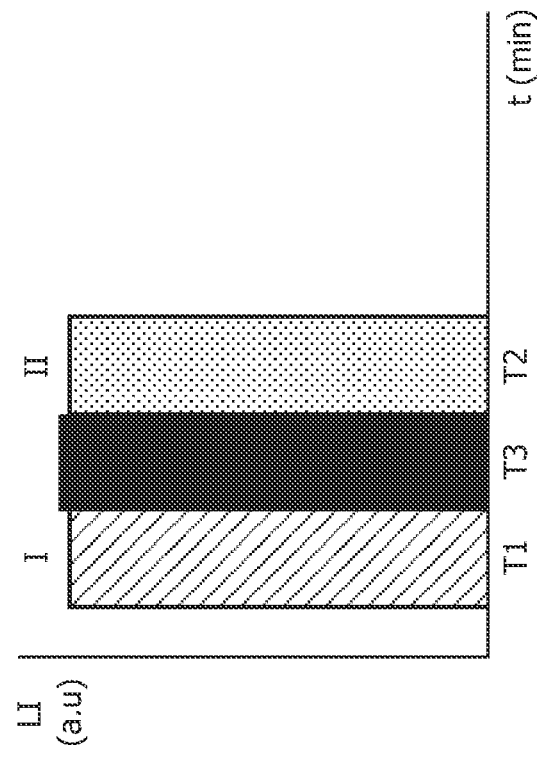

FIG. 2E shows a time diagram wherein first and second illumination outputs I, II are alternated. The first time intervals T1 increase in duration (e.g. 15 seconds, 30 seconds, 1 minute), whereas the light intensity of the first illumination output I decreases.

Figure 2F:
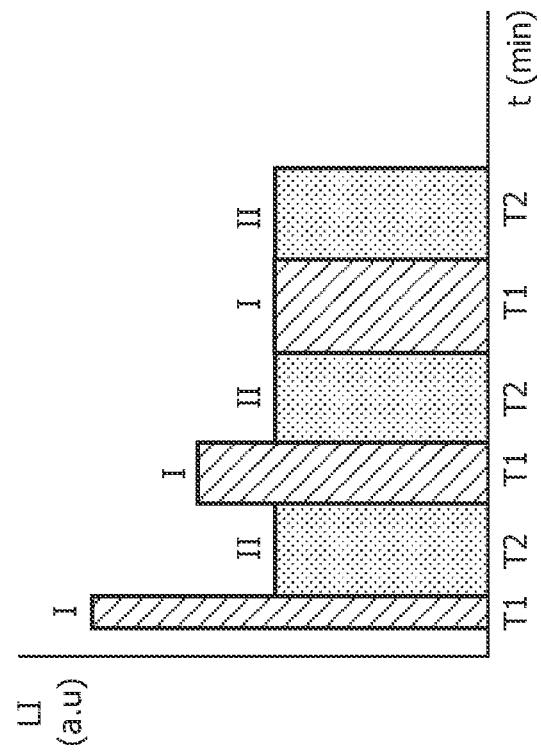

Finally, in FIG. 2F, a time diagram is shown wherein between the first illumination output I and the second illumination output II, the human being M is exposed to darkness during a third period T3. Darkness allows for re-adaptation to a dark-adapted retinal state where the photoreceptor sensitivity is increased, provoking a stronger response to a given light stimulus. Controller 2 is programmed such that both light sources 3A and 3B are not activated during T3, whereas illumination device 1 is operated in a substantially dark environment.

Various applications of the illumination device 1 have been considered. An example includes people working irregular shifts (pilots, truck drivers), who need to wait some time after obligatory rest periods to become sufficiently alert to perform their tasks. The present recommendation for e.g. pilots is to wait for 30 minutes after waking up before taking over their duty. The disclosed illumination device 1 could reduce the waiting time, and therefore the personnel costs. The invention is also advantageous for police officers and the military: the invention allows for a rapid reduction of sleep inertia after sleep so it minimizes the delay (or danger) in immediate operations. Automotive lighting has also been considered: in-car exposure to the illumination device 1 can be used to boost night driver alertness. Also, control rooms requiring 24-hour operations and night shift work for which sustained alertness is essential are possible application areas.

The illumination device 1 can also be applied in office lighting to improve early morning activity and/or reduce after-lunch dip. Hospital lighting is an area of application to reduce sleep inertia of medical staff upon nocturnal wake-up. Furthermore, care home lighting, improve daytime activity and/or reduce day-time napping of elderly or healthcare patients to improve nocturnal sleep-duration and sleep-quality have been envisaged.

The invention claimed is:

1. An illumination device arranged for reducing sleep inertia and/or for increasing alertness of a human being comprising:
    one or more light sources for generating a first illumination output and a second illumination output, wherein the first illumination output comprises:
    light with a dominant wavelength in the range of 590-770 nm, or
    white light with a color temperature below 4100 K,
    and the second illumination output comprises:
    light with a dominant wavelength in the range of 400-560 nm, or
    white light with a color temperature above 4900 K; and
    a controller configured for controlling said one or more light sources to implement an exposure of said eye of said human being to said first illumination output during a first time interval and to implement an initial exposure of said eye to said second illumination output during a second time interval such that said second illumination output is introduced essentially instantaneously, wherein said second time interval terminates at a later point in time than said first time interval, wherein at least one of the first and second time interval is equal to or less than 60 seconds.

2. The illumination device according to claim 1, wherein said dominant wavelength of said first illumination output is in the range of 600-650 nm and said dominant wavelength of said second illumination output is in the range of 450-500 nm.

3. The illumination device according to claim 1, wherein at least one of said first and second time intervals has a duration in the range of 1 millisecond-10 seconds.

4. The illumination device according to claim 1, wherein said controller is configured for controlling said one or more light sources for alternating said first illumination output and said second illumination output such that said alternated first illumination output is implemented during successive first time intervals and said alternated second illumination output is implemented during successive second time intervals.

5. The illumination device according to claim 1, wherein said controller is configured for controlling said one or more light sources for repeating said first illumination output during successive first time intervals within said second time interval.

6. The illumination device according to claim 1, wherein at least one of said first and second illumination output comprises substantially monochromatic light.

7. The illumination device according to claim 1, wherein the controller is configured for controlling said one or more light sources to essentially instantaneously transition between said first illumination output and said second illumination output.

8. An illumination device arranged for reducing sleep inertia and/or for increasing alertness of a human being comprising:
    one or more light sources for generating a first illumination output and a second illumination output, wherein the first illumination output comprises:
    light with a dominant wavelength in the range of 590-770 nm, or
    white light with a color temperature below 4100 K,
    and the second illumination output comprises:
    light with a dominant wavelength in the range of 400-560 nm, or
    white light with a color temperature above 4900 K; and
    a controller configured for controlling said one or more light sources to expose said eye of said human being to said first illumination output during a first time interval and to said second illumination output during a second time interval, wherein said second time interval terminates at a later point in time than said first time interval, and wherein at least one of said first and second time intervals are less than one second.

9. The illumination device according to claim 8, wherein at least one of said first and second time intervals are equal to or less than 100 milliseconds.

10. The illumination device according to claim 8, wherein at least one of said first and second time intervals are equal to or less than 50 milliseconds.

11. An illumination device arranged for reducing sleep inertia and/or for increasing alertness of a human being comprising:
- one or more light sources for generating a first illumination output and a second illumination output, wherein the first illumination output comprises:
- light with a dominant wavelength in the range of 590-770 nm, or
- white light with a color temperature below 4100 K, and the second illumination output comprises:
- light with a dominant wavelength in the range of 400-560 nm, or
- white light with a color temperature above 4900 K; and
- a controller configured for controlling said one or more light sources to expose said eye of said human being to said first illumination output during a first time interval and to said second illumination output during a second time interval, wherein said second time interval terminates at a later point in time than said first time interval, wherein at least one of the first and second time interval is equal to or less than 60 seconds, and wherein said controller is configured for controlling said one or more light sources to temporarily and essentially stop illumination output to generate a dark third time interval between said first illumination output and said second illumination output.

12. A method for obtaining at least one of the following effects for a human being:
- reducing sleep inertia;
- increasing alertness;
- phase shifting; or
- therapeutic effect;

the method comprising the steps of:
- implementing an exposure, during a first time interval, of an eye of said human being to a first illumination output comprising
- light with a dominant wavelength in the range of 590-770 nm, or
- white light with a color temperature below 4100 K
- implementing an initial exposure, during a second time interval, of the eye of said human being to a second illumination output such that said second illumination output is introduced essentially instantaneously, said second illumination output comprising:
- light with a dominant wavelength in the range of 400-560 nm, or
- white light with a color temperature above 4900 K said second time interval terminating at a later point in time than said first time interval.

13. The method according to claim 12, comprising the step of alternating said first and second illumination output such that said alternated first illumination output is implemented during successive first time intervals and said alternated second illumination output is implemented during successive second time intervals.

14. The method according to claim 12, comprising the step of repeating said first illumination output during successive first time intervals within said second time interval.

15. The method according to claim 12, comprising the steps of:
- temporarily stopping said first and second illumination output during a third time interval;
- subsequently exposing said eye to at least said second illumination output during said second time interval.

16. The method according to claim 12, wherein at least one of said first and second time intervals is equal to or less than 60 seconds.

17. The method according to claim 12, wherein at least one of the first and second time intervals is equal to or less than 50 milliseconds.

18. The method according to claim 12, further comprising essentially instantaneously transitioning between said first illumination output and said second illumination output.

* * * * *